United States Patent
Hynecek

(10) Patent No.: US 8,710,420 B2
(45) Date of Patent: Apr. 29, 2014

(54) IMAGE SENSOR PIXELS WITH JUNCTION GATE PHOTODIODES

(75) Inventor: Jaroslav Hynecek, Allen, TX (US)

(73) Assignee: Aptina Imaging Corporation, George Town (KY)

( * ) Notice: Subject to any disclaimer, the term of this patent is extended or adjusted under 35 U.S.C. 154(b) by 0 days.

(21) Appl. No.: 13/450,154

(22) Filed: Apr. 18, 2012

(65) Prior Publication Data

US 2013/0153973 A1     Jun. 20, 2013

Related U.S. Application Data

(60) Provisional application No. 61/577,340, filed on Nov. 8, 2011.

(51) Int. Cl.
*H01L 27/00*     (2006.01)

(52) U.S. Cl.
USPC .............. 250/208.1; 250/214.1; 257/292; 257/E27.154

(58) Field of Classification Search
CPC .......... H01L 27/14603; H01L 27/14609; H01L 27/14643; H01L 27/14679; H01L 27/1464
USPC ........... 257/223, 230, 233, 258, 292, 369, 257/E27.133, E27.131, E27.132, E27.148, 257/E31.001, E27.154; 348/299; 250/208.1, 214 A, 214 R, 214.1, 214 SW
See application file for complete search history.

(56) References Cited

U.S. PATENT DOCUMENTS

| | | | |
|---|---|---|---|
| 5,625,210 A | 4/1997 | Lee | |
| 5,712,498 A * | 1/1998 | Reich et al. | 257/256 |
| 6,188,093 B1 | 2/2001 | Isogai et al. | |
| 6,797,935 B2 * | 9/2004 | Kaya et al. | 250/214.1 |
| 7,417,268 B2 * | 8/2008 | Cazaux et al. | 257/225 |
| 7,999,342 B2 * | 8/2011 | Hsu et al. | 257/447 |
| 8,163,591 B2 * | 4/2012 | Park et al. | 438/72 |
| 8,334,491 B2 * | 12/2012 | Bogaerts et al. | 250/208.1 |
| 2003/0090584 A1 | 5/2003 | Goto | |
| 2007/0187732 A1 | 8/2007 | Goto | |
| 2007/0290242 A1 * | 12/2007 | Katsuno et al. | 257/292 |
| 2008/0258182 A1 * | 10/2008 | Agarwal et al. | 257/256 |
| 2008/0283886 A1 * | 11/2008 | Hynecek | 257/292 |
| 2008/0296643 A1 | 12/2008 | Inoue et al. | |
| 2010/0148037 A1 * | 6/2010 | Bogaerts et al. | 250/214 A |
| 2012/0273653 A1 * | 11/2012 | Hynecek et al. | 250/208.1 |
| 2012/0273654 A1 * | 11/2012 | Hynecek et al. | 250/208.1 |

FOREIGN PATENT DOCUMENTS

| | | | | |
|---|---|---|---|---|
| EP | 2037672 | | 3/2009 | |
| KR | 2005-0121441 | * | 12/2005 | H04N 5/335 |

* cited by examiner

*Primary Examiner* — Marvin Payen
*Assistant Examiner* — Victor Barzykin

(57) ABSTRACT

Image sensor pixels are provided having junction gate photodiodes. A group of pixels may have a shared floating diffusion region and a shared source-follower transistor. The source-follower transistor may be a JFET source-follower with a gate that forms the floating diffusion region. The JFET source-follower may be a vertical or lateral JFET. A reset diode may be forward-biased to reset the floating diffusion region. Each pixel may have a JFET that serves as a charge transfer barrier between the junction gate photodiode and the floating diffusion region. The charge transfer barrier JFET may be a lateral JFET. The image sensor pixels may be formed without any metal-oxide-semiconductor devices.

19 Claims, 7 Drawing Sheets

IMAGE SENSOR PIXELS WITH JUNCTION GATE PHOTODIODES

This application claims the benefit of provisional patent application No. 61/557,340, filed Nov. 8, 2011, which is hereby incorporated by reference herein in its entirety.

BACKGROUND

This invention relates generally to image sensors, and more particularly, to back-side illuminated (BSI) image sensors.

Typical image sensors sense light by converting impinging photons into electrons that are integrated (collected) in sensor pixels. After completion of an integration cycle, collected charge is converted into a voltage, which is supplied to output terminals of the sensor.

For active pixel image sensors, charge-to-voltage conversion is performed in the pixels themselves. Pixel signals can be transferred as analog signals from individual pixels to output terminals of the image sensor. Alternatively, an analog pixel signal can be converted into a digital signal before it is transferred to the output terminals of the image sensor.

Various pixel addressing and scanning schemes can be used to transfer pixel signals from the individual pixels to the image sensor output terminals. Typically, each pixel has a buffer amplifier, such as a source follower (SF) transistor, which can drive sense lines that are connected to the pixels by suitable addressing transistors.

After pixel signals have been transferred out from the pixels, the pixels are reset in order to be ready for the accumulation of new charge. In pixels that have floating diffusion (FD) nodes that serve as charge detection nodes, the reset can be accomplished by momentarily turning on a reset transistor that conductively connects the floating diffusion node to a reference voltage supply, which is typically a pixel drain node. Resetting a pixel removes collected charge in the floating diffusion node of the pixel.

However, pixel reset may be accompanied by noise called reset noise, also known as kTC noise. Techniques such as correlated double sampling (CDS) signal processing techniques are used to reduce kTC noise in the signal. Typical active pixel sensors that utilize CDS signal processing techniques usually have three transistors per pixel (3T pixels) or 4 transistors per pixel (4T pixels). Some of the pixel transistors can be shared amongst several pixels.

A cross-sectional view of a conventional pixel 100 is shown in FIG. 1. Pixel 100 may be formed in a substrate 101. A p+ type layer 102 is deposited on a back surface of substrate 101, which prevents generation of excessive dark current by interface states. A p-type epitaxial layer 115 is formed over p+ layer 102. A photodiode PD (in region 96) is formed by n-type region 108 (also known as a charge storage layer) and p+ type pinning layer 107.

Pixel 100 has a transfer gate 110 that receives transfer signal Tx. Transfer gate Tx 110 is formed from doped polysilicon. An oxide layer 109 isolates transfer gate 110 from epitaxial layer 115. A masking oxide 111 is formed over transfer gate 110 that serves as a patterning hard mask as well as an additional blocking mask for ion plantation. Sidewall spacers 116 can help to control mutual edge positions of p+ type layer 107 and n-type region 108. Floating diffusion 104 is formed in p-well 103 and receives charge signal from PD.

P+ type regions 105 and 106 provide isolation between pixels and can be connected to ground GND. Inter-level (IL) oxide layers 112 are used for isolation of multi-level metal wiring and interconnect. Metal vias 114 in contact holes 113 connect pixel active circuit components such as isolation regions 105 and 106, transfer gate 110, and floating diffusion 104 to metal wiring.

Transfer gate Tx 110, having a length as marked by arrows 98, occupies a large portion of valuable area of pixel 100. Transistors such as a source-follower (SF) transistor, reset transistor, and addressing transistor, while not shown in FIG. 1, also occupy valuable pixel area.

It would be desirable to have improved pixel circuits that are having less transistor gate surface area in order to maximize pixel area that is used for charge storage, thereby increasing the pixel charge storage capacity.

DETAILED DESCRIPTION

It is desirable to integrate pixel circuit components into single structures, preferably in a vertical direction, in order maximize pixel area occupied by the photodiode and thus maximize charge storage capacity. It is also desirable to share pixel circuit components amongst several photodiodes.

A junction gate photodiode is provided. The junction gate photodiode may be fabricated by self-aligned processing steps. The junction gate photodiode may have a source-follower transistor and a floating diffusion region integrated together into one structure. The integrated floating diffusion and source-follower transistor structure may not need a contact via to the floating diffusion. The integrated structure may be oriented in a vertical or lateral direction. Pixel reset may be accomplished with a vertically oriented diode rather than a metal-oxide-semiconductor (MOS) transistor. A junction gate photodiode pixel may be provided that does not have any MOS transistors. A junction gate photodiode pixel that does not have MOS gate structures may have increased sensor reliability, particularly at high temperatures, reduced dark current effects, and reduced random telegraph signal (RTS) noise. Pixel radiation hardness may also be increased, particularly for ionizing radiation.

Figure 1:
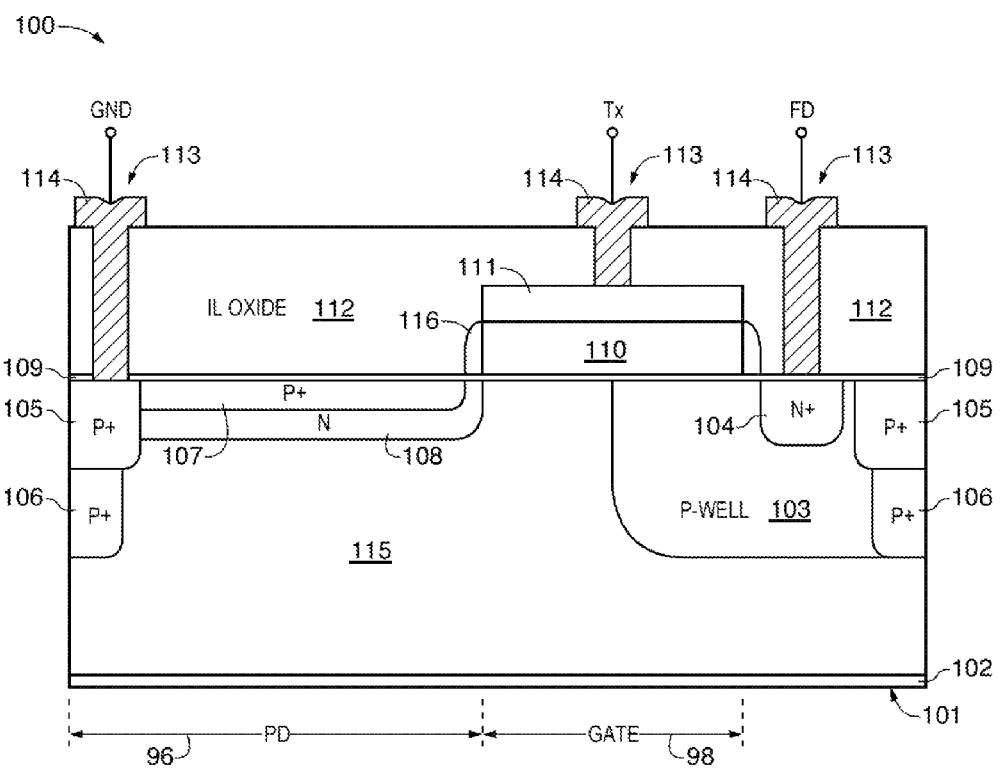
FIG. 1 is a cross-sectional view of a conventional pixel having metal-oxide-semiconductor transistors.
Figure 2:
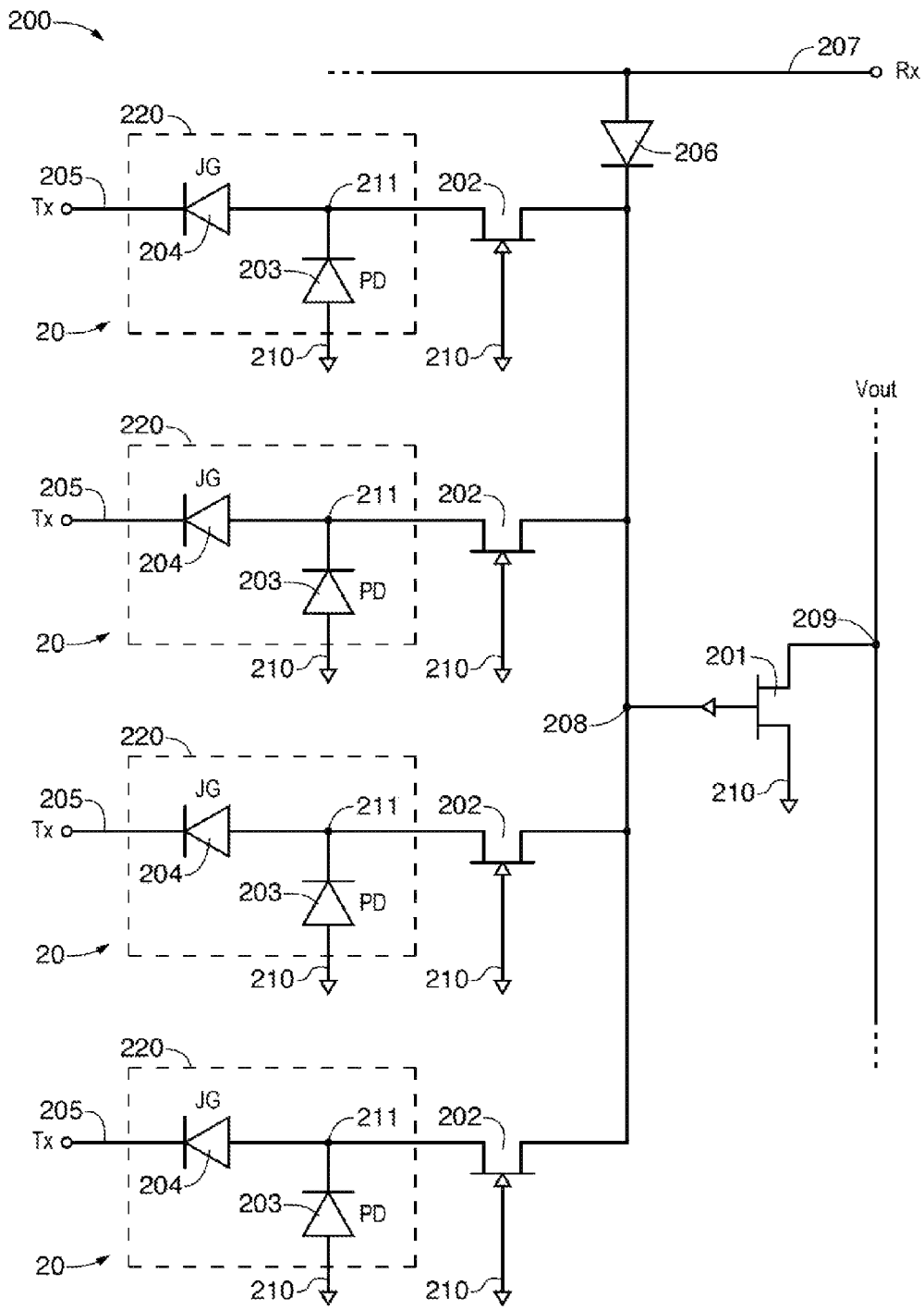
FIG. 2 is an illustrative circuit diagram of a group of four pixels having junction gate photodiodes in accordance with an embodiment of the current invention.

An illustrative circuit diagram of pixels having junction gate photodiodes is shown in FIG. 2. Pixel circuit 200 of FIG. 2 may have pixels 20. In the example of FIG. 2, pixel circuit 200 is a group of four pixels 20 that share pixel circuitry such as junction gate field-effect transistor (JFET) 201 and reset diode 206. In general, one pixel, two pixels, three pixels, four or more pixels, or any suitable number of pixels may share pixel circuitry. A pixel array in an image sensor may contain pixel circuits 200 arranged in rows and columns. A pixel array may have thousands of pixels, millions of pixels (megapixels), or more.

Each pixel 20 may have a photodiode such as junction gate photodiode 220. Junction gate photodiode 220 may have junction gate (JG) diode 204 and photodiode (PD) 203. Junction gate diode 204 may have a gate region that is n+ type. The gate region of junction gate diode 204 may be connected to transfer signal line 205. The gate region of junction gate diode 204 may be known as a junction gate. Incident light on photodiode 203 may generate charge. Photodiode 203 and junction gate diode 204 may form a node 211, which may serve as a potential well for storing photo-generated charge. Node 211 may be known as a charge storage well.

Junction gate diode 204 may be connected to line 205 which receives transfer signal Tx. Each pixel 20 may have a JFET 202 connected to node 211. JFET 202 may be a lateral n-channel JFET having a gate connected to ground terminal 210. JFET 202 may form a charge transfer barrier between charge storage node 211 and a shared floating diffusion node 208 that is shared amongst pixels 20 in pixel circuit 200.

Pixel circuit 200 of FIG. 2 may have a shared JFET such as JFET 201. JFET 201 may be known as a source-follower (SF) JFET. JFET 201 may be a vertical or lateral JFET. JFET 201 may be a p-channel JFET. JFET 201 may have a drain connected to ground terminal 210 and a source connected to column line 209, also known as an output line. P-channel JFET 201 may have a gate that is doped n-type. The n-type gate of JFET 201 may form floating diffusion node 208. Floating diffusion node may also be known as a charge detection node. Floating diffusion node 208 formed from the gate of JFET 201 may have no need for a contact via to metal wiring.

Floating diffusion node 208 may be reset with a diode such as reset diode 206. Reset diode 206 may be connected to a reset line 207. When reset line 207 is driven high, diode 206 is forward-biased and floating diffusion node 208 may be reset to a reset voltage. After floating diffusion node 208 is reset, reset line 207 is driven low, reverse-biasing diode 206. Floating diffusion node 208 is then able to receive and hold photo-generated charge.

During an integration period, junction gate diode 204 is reverse-biased by a high voltage on addressing line 205. Photodiodes 203 generate photo-generated charge from incident light and the photo-generated charge is stored at node 211. The photo-generated charge is separated by a barrier formed by JFET 202 from floating diffusion node 208.

Following the integration period, addressing lines 205 are pulsed low, which transfers photo-generated charge from node 211 to floating diffusion node 208. The transfer of photo-generated charge from node 211 to floating diffusion node 208 may occur sequentially for pixels 20 in pixel circuit 200.

The photo-generated charge on floating diffusion node 208 changes the source voltage of the source-follower JFET that may be sampled after charge transfer from each one of pixels 20. After each sensing, node 208 may be reset. Alternatively, photo-generated charge from one, two, three, or four pixels 20 may be summed on floating diffusion node 208 before floating diffusion node 208 is reset. Source-follower JFET 201 may output a signal voltage Vout to column line 209. Sampled charge may be stored in reference storage place of a correlated double sampling (CDS) circuit.

In the example of FIG. 2, pixel circuit 200 has 1.25 JFETs per pixel 20, which may have the advantage of being space-efficient. If desired, pixel circuit 200 may be formed with a different JFET per pixel ratio, especially if pixel circuit 200 has a different number of pixels 20 than in the example of FIG. 2.

Figure 3:
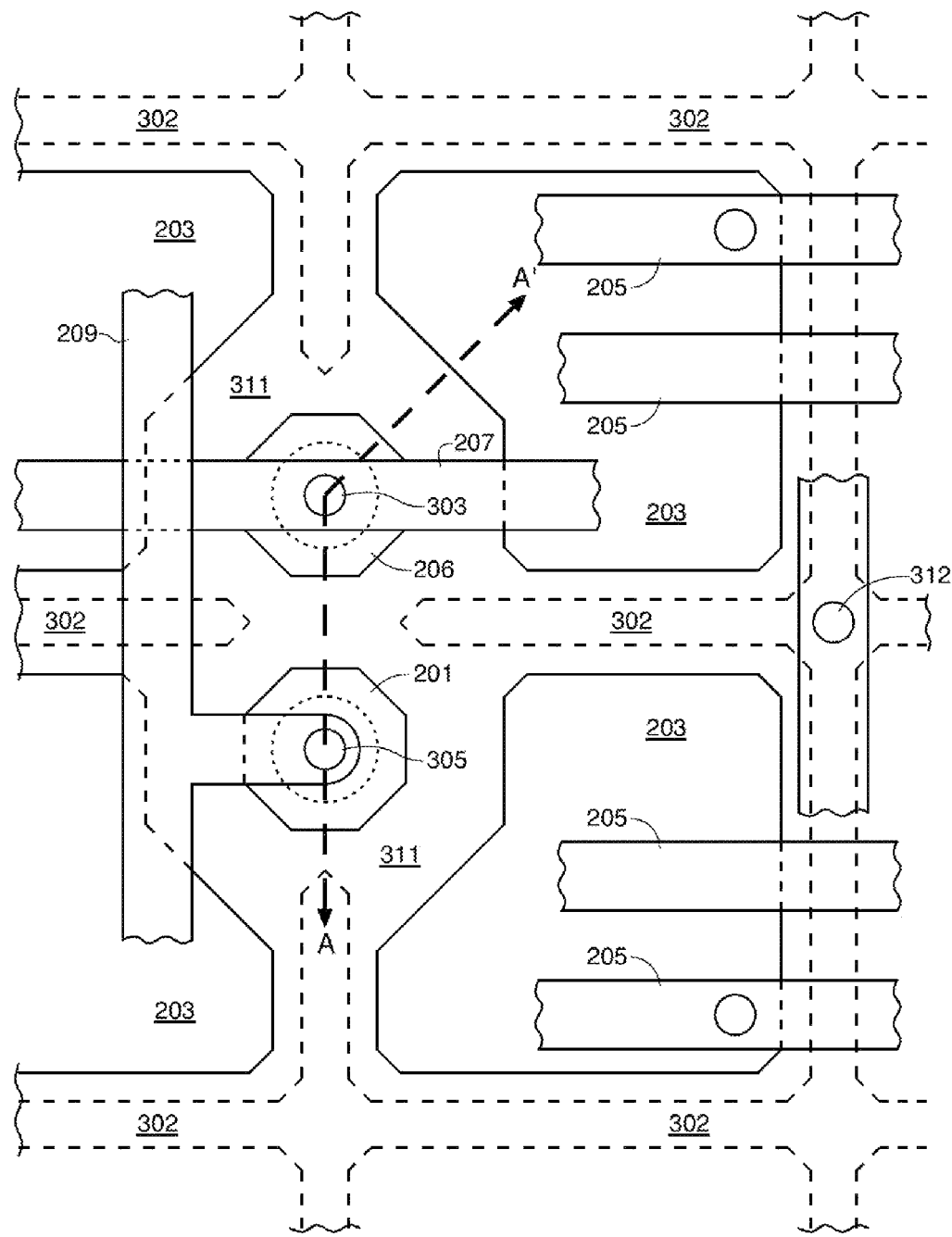
FIG. 3 is an illustrative layout for a pixel having a vertical JFET source-follower in accordance with an embodiment of the current invention.

An illustrative layout topology for pixel circuit 200 is shown in FIG. 3. Four junction gate photodiodes 203 may be formed around reset diode 206 and source-follower JFET 201. Areas outside of regions 203, 206, and 201 may be p+ type ground that is connected to ground contact via 312. Column line 209 may be connected to source-follower JFET 201 through via 305. Row line 207 may supply a reset signal to reset diode 206 through via 303. Lines 205 may supply transfer gate voltages Tx. Pixel isolation implants may be formed in regions 302. JFETs 202 that form charge transfer barriers may be formed in regions 311.

A 4-shared pixel layout is shown in FIG. 3 in which four pixels share a common reset diode 206 and source-follower JFET 201. If desired, the layout of FIG. 3 may be adapted for 2-shared pixel structure, a no-shared pixel structure, or an 8-shared pixel structure. In the case of an 8-shared pixel structure, source-follower JFET 201 may be formed in a different group of four photodiodes 203 than reset diode 206. For an 8-shared pixel structure, an n+ contact may be provided to the floating diffusion node formed by the gate of source-follower JFET 201.

A cross-sectional view through line A-A' of FIG. 3 at different stages of processing is shown in FIGS. 4A-4D. Line A-A' of FIG. 3 intersects JFET 201 and reset diode 206 and a shared junction gate photodiode 220, which are labeled accordingly in FIGS. 4A-4D. The diagram of FIG. 4A-4D may represent a cross section of portion of pixel 200 that is located in a top layer of p-type doped epitaxial substrate such as substrate 401 in FIGS. 4A-4D. Pixel circuit 200 may also have bulk regions of substrate 401 where photoelectrons are generated and a back interface having a p+ doping layer that are not shown in FIG. 4A-4D. If desired, pixel 200 may be formed directly in a bulk substrate.

Figure 4A:
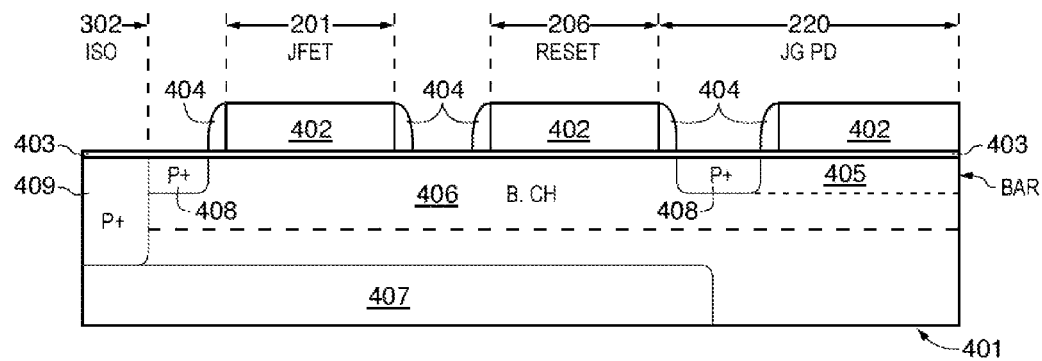
FIG. 4A is a cross-sectional view of an illustrative first fabrication stage of a pixel having a vertical JFET source-follower in accordance with an embodiment of the current invention after several processing steps have been already implemented.

As shown in FIG. 4A, a substrate may be provided such as p-type doped epitaxial substrate 401. Substrate 401 may have a BTP (bottom p layer) p-type doped layer 407. Layer 407 may help divert photogenerated electrons to potential storage well under junction gate. Layer 406 may be a buried channel n-type doped layer 406 (BCH). Layer 405 may be a p-type doped blocking layer 405 (BAR). Substrate 401 may have pixel isolation implants 409 that correspond with implant regions 302 of FIG. 3. An oxide layer 403 may be formed over substrate 401.

Layers 402 may be temporary layers that define future active device regions. Layers 402 may be formed from polysilicon or other suitable materials. Sidewall oxide spacers 404 may be formed at the edges of polysilicon regions 402. P+ type doped pinning implants 408 in substrate 401 may have sizes that are defined by sidewall oxide spacers 404.

P+ type doped pinning implant 408 and n-type doped layer 406 may form a photodiode such as photodiode 203 in FIGS. 2 and 3. N-type doped layer 406 may serve as a charge storage well such as node 211 in FIG. 2. P-type layer 405 and n+ type layer 413 in FIG. 4B may form a junction gate diode such as junction gate diode 204 of FIG. 2. N+ type layer 413 may be known as a gate region for junction gate PD.

Figure 4B:
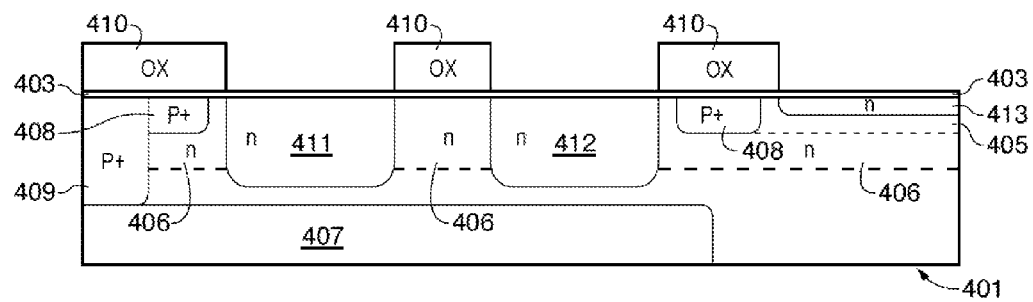
FIG. 4B is a cross-sectional view of an illustrative subsequent fabrication stage of a pixel having a vertical JFET source-follower in accordance with an embodiment of the current invention.

As shown in FIG. 4B, layer 402 may be removed. Oxide layer 410 may be subsequently deposited on the structure. Oxide layer 410 may serve as a self-aligned mask for implantation of n-type doped PD junction gate 413, n-type doped vertical JFET gate 411, and n-type doped reset diode region. Additional photoresist masks over oxide layer 410 may be used to select varying doping dosages for regions 413, 411, and 412. The self-aligned processing precisely defines a distance between p+ type doped pinning implant 408 and n-type doped junction gate implant 413, which is a distance that defines gate breakdown voltage. Self-aligned processing also improves pixel-to-pixel uniformity and improves sensor fixed pattern noise.

Figure 4C:
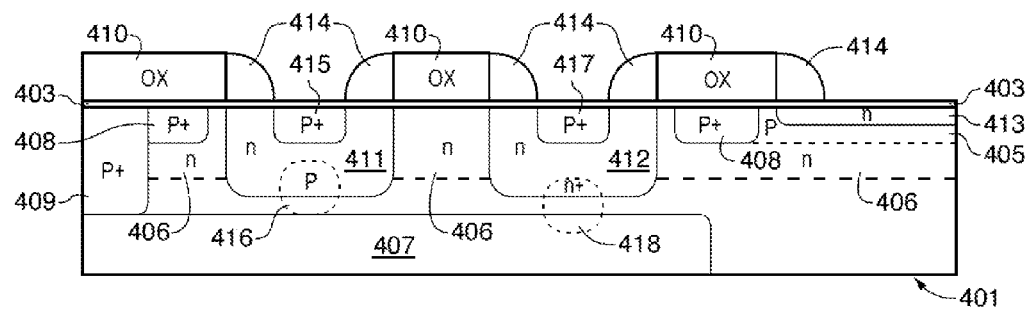
FIG. 4C is a cross-sectional view of an illustrative subsequent fabrication stage of a pixel having a vertical JFET source-follower in accordance with an embodiment of the current invention.

As shown in FIG. 4C, nitride spacers 414 may be deposited. Nitride spacers 414 may form a self-aligned mask for implantation of p+ type doped source 415 of JFET 201 and p+ type doped region 417 of reset diode 206. P type JFET channel 416 of JFET 201 and n+ type doped charge recombination region 418 of reset diode 206 may be deposited.

Figure 4D:
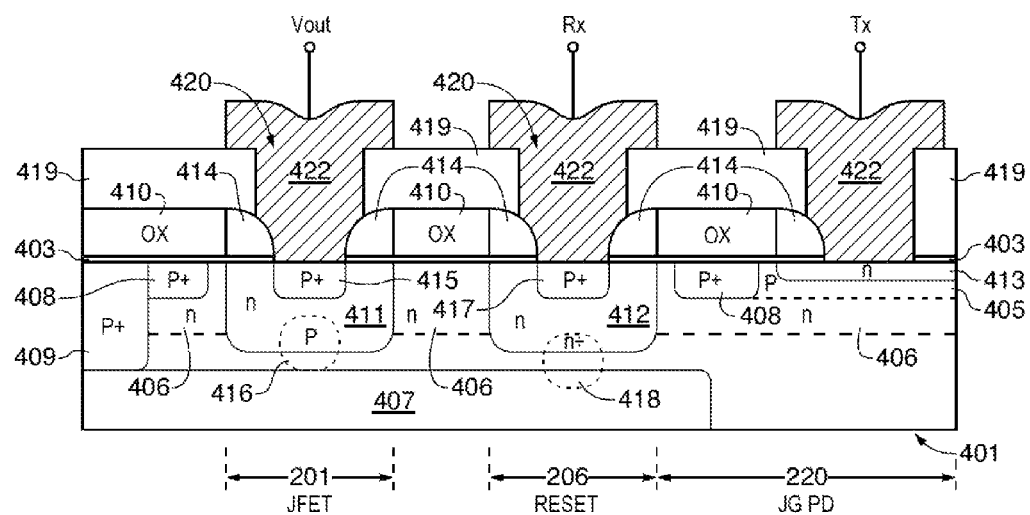
FIG. 4D is a cross-sectional view of an illustrative subsequent fabrication stage of a pixel having a vertical JFET source-follower in accordance with an embodiment of the current invention.

As shown in FIG. 4D, inter-level oxide layers 419 may be deposited. Metal vias 422 maybe formed in holes 420 of oxide layers 419. Nitride spacers 414 may provide self-alignment of vias 422 to regions 415 and 417 without need for precise alignment of holes 420.

In the example of FIGS. 4A-4D, regions 411 and 412 may be electrically connected by buried channel layer 406. For an 8-shared pixel layout, connections between regions 411 and 412 may be implemented by wiring above substrate 401. In the example of FIGS. 4A-4D, JFET 201 and reset diode 206 have separate n-type regions 411 and 412, respectively, that are electrically connected by buried channel layer 406. If desired, JFET 201 and reset diode 206 may have a same n-type region, in which case reset diode 206 may be said to be integrated into JFET 201.

A potential barrier in a region under n+ type junction gate 413 may be adjusted by a suitable p-type doping level such that overflow charge from the potential well located under n+ type junction gate 413 flows vertically into n+ type junction gate 413, preventing blooming into neighboring pixels.

Figure 5:
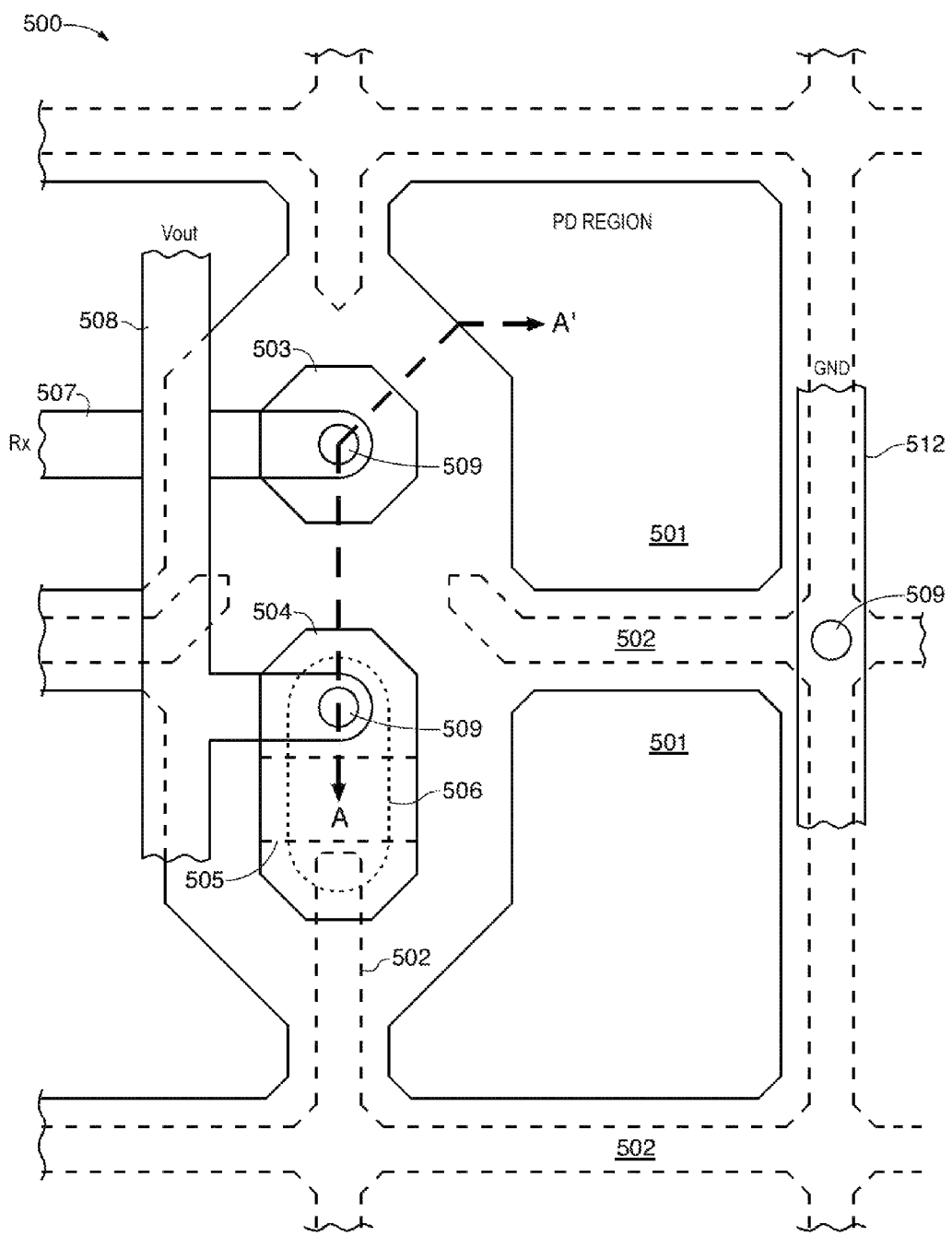
FIG. 5 is an illustrative layout for a pixel having a lateral JFET source-follower in accordance with an embodiment of the current invention.

FIG. 5 is a top view of an illustrative topology for pixel 200 for an example when source follower JFET 201 of FIG. 2 is a lateral JFET. Topology 500 of FIG. 5 is for a 4-shared junction gate photodiode pixel group. Region 501 may be an outline of an n+ doped junction photodiode gate having a charge storage well underneath. Region 503 may contain a vertical reset diode 206 (see, e.g., FIG. 2). Region 504 may contain source follower JFET 201. JFET 201 may have a channel formed in region 506 and an n+ gate formed in region 505. Region 505 may be connected to an n-well implanted in JFET region 504 and reset diode region 503. Region 506 may be p-type doped and connects to p+ doped pixel isolation region 502. Isolation region 502 may be connected to a ground voltage supplied by column metal bus line 512 through metal via 509. Metal vias 509 may have a self-aligned p+ doping underneath to provide a low resistance connection. Bus line 507 may supply a voltage Rx through via 509 to p+ doping region below via 509. Column bus line 508 may convey an output signal from a source of JFET 201 in region 504 to peripheral circuits for processing.

Figure 6A:
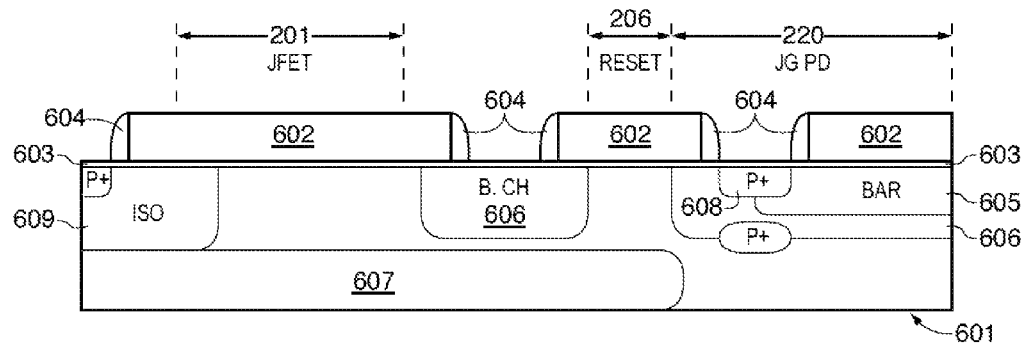
FIG. 6A is a cross-sectional view of an illustrative fabrication stage of a pixel having a lateral JFET source-follower in accordance with an embodiment of the current invention.
Figure 6B:
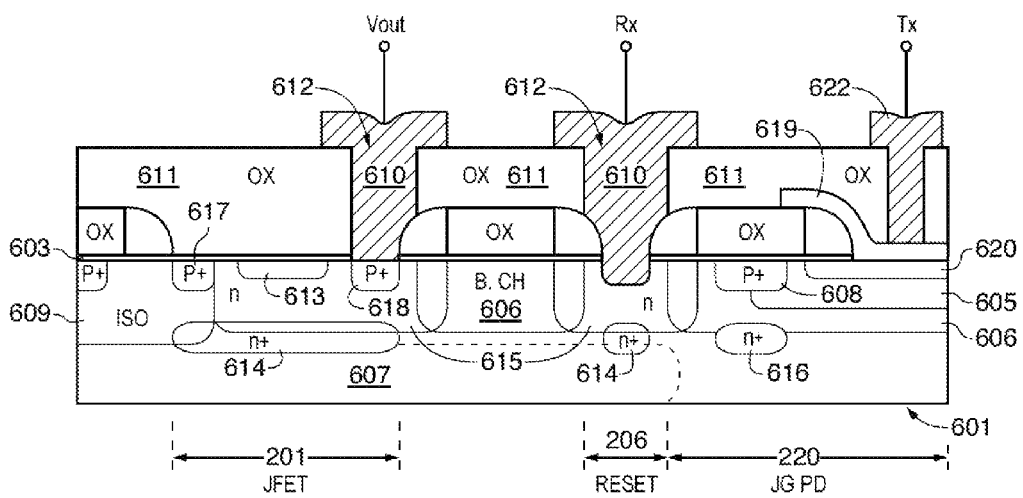
FIG. 6B is a cross-sectional view of an illustrative subsequent fabrication stage of a pixel having a lateral JFET source-follower in accordance with an embodiment of the current invention.

FIGS. 6A and 6B show the pixel cross sections after several processing steps have been implemented that may be used to form topology 500 of FIG. 5 having a lateral source follower JFET. FIGS. 6A and 6B may represent a cross-section view through line A-A' of FIG. 5. FIGS. 6A and 6B show a top layer of p-type doped epitaxial substrate 601. A remainder of substrate 601, where photo-electrons are generated, and a back interface having a p+ type doping layer is not shown.

As shown in FIG. 6A, an oxide layer 603 may be formed over substrate 601. Temporary polysilicon regions 602 are patterned over oxide layer 603. Sidewall oxide spacers 604 define the sizes of p+ type doping pinning implants 608. If desired, regions 602 may be formed of materials other than polysilicon. Prior to deposition of layer 602, BTP p-type doped layer 607 is formed that diverts photoelectrons to the potential storage well under the junction gate photodiode 203. Buried channel n-type doped layer 606 and the p-type doped blocking layer 605 under the junction gate 620 (see, e.g., FIG. 6B) are also implanted before layer 602 is deposited. Pixel isolation implant 609 is also formed in this invention embodiment.

As shown in FIG. 6B, metal vias 610 are deposited through contact holes 612 in interlevel oxide layers 611. Gate region 613 of JFET 202 is deposited in n-well 615. The bottom of n-well 615 may be implanted with an n+ doped region 614 that may prevent complete depletion of n-well 615. Reset diode 202 also has an n-well region 615 and an n+ region 614. A charge transfer region formed by JFET 202 contains deep p+ implant 616 which prevents potential modulation from an adjacent junction gate photodiode when the bias of the junction gate is changed. JFET 202 has p+ source region 618 that is connected to metal via 610. JFET 202 has p+ drain region 617 that is connected to p+ pixel isolation region 609 and is connected to a ground voltage.

The n+ doped junction gate region 620 may be covered by a thin metal layer 619 that can be used later in the processing to form self-aligned metal silicide. Suitable metals for metal layer 619 may include titanium, tungsten, or nickel. The metal silicide act as a mirror on top of the photodiode that reflects the light that has not been fully absorbed in the silicon bulk when the device is illuminated from the back side. This improves quantum efficiency. Silicide thickness can be thin and provides an easier contact to metal via 622. Metal layer 619 is optional and may also be used in the example of FIG. 4D.

Junction diode pixels in the examples of FIG. 2-6 have an inherent vertical blooming control, since overflow charge can be drained directly to n+ junction gates such as n+ junction gate 413 (see, e.g., FIG. 4D) or 620 (see, e.g., FIG. 6B). The interface generated dark current is automatically drained to junction gate 413 or 620 and is not collected in the charge storage well under the gate. This results in significant performance advantages as compared to conventional CMOS pixel technology, especially for sensors with sub-micron pixel sizes.

Junction gate photodiode pixels in the examples of FIG. 2-6 have a high well capacity that is achieved by reducing a gate length of the charge transfer region and by integrating floating diffusion and vertical JFET together in one structure without the need for a metal contact. The pixels may be fabricated using self-aligned processing steps for the critical geometries, which improves uniformity and thus the sensor fixed pattern noise. Having no metal-oxide-semiconductor structures may improve sensor reliability and operation at high temperatures.

Various embodiments have been described illustrating image sensor pixels that are having junction gate photodiodes. A group of pixels may have a shared floating diffusion region and a shared source-follower transistor. The shared source-follower transistor may be a JFET source-follower with a gate that forms the floating diffusion region. The JFET source-follower may be a vertical or lateral JFET. A shared reset diode may be connected to the shared floating diffusion region. The reset diode may be forward-biased to reset the floating diffusion region. A group of pixels sharing pixel circuitry may be a group of four pixels, eight pixels, or any suitable number of pixels.

Each pixel may have a JFET that serves as a charge transfer barrier between the junction gate photodiode and the shared floating diffusion region. The charge transfer barrier JFET may be a lateral JFET. The charge transfer barrier JFET may have a gate connected to a ground. Incident light may generate charge that is stored in a charge storage node in the junction gate photodiode. A transfer signal on a transfer signal line connected to the junction gate photodiode may be pulsed to transfer charge from the charge storage node to the shared floating diffusion region. The shared floating diffusion region may receive and reset charge from one pixel before receiving charge from a second pixel. Alternately, the floating diffusion region may receive and sum charge signals from multiple pixels.

The image sensor pixels may be formed without any metal-oxide-semiconductor devices.

The foregoing is merely illustrative of the principles of this invention which can be practiced in other embodiments.

What is claimed is:

1. Pixels on a pixel array, comprising:
    a plurality of junction gate photodiodes;
    a plurality of junction gate field-effect transistors each coupled to a respective one of the junction gate photodiodes;
    a junction gate field-effect transistor source-follower having a gate connected to the plurality of junction gate field-effect transistors, wherein the gate forms a floating diffusion node for the pixel; and
    a reset diode configured to reset the floating diffusion node in the pixel.

2. The pixels defined in claim 1, wherein the junction gate field-effect transistor source-follower comprises a vertical p-channel junction gate field-effect transistor source-follower.

3. The pixels defined in claim 1, wherein the junction gate field-effect transistor source-follower comprises a lateral p-channel junction gate field-effect transistor source-follower.

4. The pixels defined in claim 1, wherein the plurality of junction gate field-effect transistors comprise a plurality of lateral n-channel junction gate field-effect transistors.

5. The pixels defined in claim 1, wherein the plurality of junction gate photodiodes comprises at least four junction gate photodiodes and wherein the plurality of junction gate field-effect transistors comprises at least four junction gate field-effect transistors.

6. The pixels defined in claim 1, wherein the gate of the junction gate field-effect transistor source-follower comprises an n+ type gate.

7. The pixels defined in claim 1, wherein the pixels comprise back-side illuminated pixels and wherein each junction gate photodiode in the plurality of junction gate photodiodes has a metal silicide layer that serves to reflect light.

8. A pixel array having pixels, comprising:
    a junction gate field-effect transistor source-follower having a gate that forms a floating diffusion node;
    a reset diode that resets the floating diffusion node; and
    a plurality of junction gate photodiodes coupled to the floating diffusion node.

9. The pixel array defined in claim 8, wherein the junction gate field-effect transistor source-follower comprises a p-channel junction gate field-effect transistor source-follower and wherein the gate comprises an n+ type gate.

10. The pixel array defined in claim 8, further comprising a plurality of junction gate field-effect transistors each coupled between a respective one of the junction gate photodiodes and the floating diffusion node, wherein the junction gate field-effect transistors in the plurality of junction gate field-effect transistors serve as charge transfer barriers.

11. The pixel array defined in claim 10, wherein the reset diode is forward-biased to reset the floating diffusion node.

12. The pixel array defined in claim 10, wherein the plurality of junction gate photodiodes comprises four junction gate photodiodes.

13. The pixel array defined in claim 10, wherein the plurality of junction gate photodiodes comprises eight junction gate photodiodes.

14. A pixel array for an image sensor, comprising:
    a plurality of pixels, wherein each pixel in the plurality of pixels comprises a junction gate photodiode;
    a junction gate field-effect transistor source-follower for the plurality of pixels, wherein the junction gate field-effect transistor source-follower has a gate that forms a floating diffusion region for the plurality of pixels and wherein the junction gate field-effect transistor source-follower is coupled to an output for the plurality of pixels; and
    a reset diode that is configured to reset the floating diffusion region.

15. The pixel array defined in claim 14, wherein the floating diffusion region is configured to receive charge from each junction gate photodiode and wherein the floating diffusion region is configured to store charge that is a sum of the charge from each of the junction gate photodiodes.

16. The pixel array defined in claim 14, wherein the floating diffusion region is configured to receive charge from a given junction gate photodiode and wherein the floating diffusion region is reset before the floating diffusion region receives charge from another junction gate photodiode.

17. The pixel array defined in claim 14, wherein the floating diffusion region is configured to receive and sum charge from at least two junction gate photodiodes before the floating diffusion region is reset.

18. The pixel array defined in claim 14, wherein each pixel in the plurality of pixels further comprises a junction gate field-effect transistor that forms a charge transfer barrier between the junction gate photodiode and the floating diffusion region, wherein the junction gate field-effect transistor has a gate connected to a ground terminal.

19. The pixel array defined in claim 14, wherein the junction gate photodiode has a charge storage well and wherein overflow flow charge from the charge storage well flows into a gate region of the junction gate photodiode which prevents blooming effects.

* * * * *